United States Patent [19]

Kramer et al.

[11] Patent Number: 5,028,139
[45] Date of Patent: Jul. 2, 1991

[54] READHEAD FOR REFLECTANCE MEASUREMENT OF DISTANT SAMPLES

[75] Inventors: Donald L. Kramer, San Juan Capistrano, Calif.; Gerald H. Shaffer, Wakarusa, Ind.

[73] Assignee: Miles Inc., Elkhart, Ind.

[21] Appl. No.: 74,073

[22] Filed: Jul. 16, 1987

[51] Int. Cl.$^5$ .............................................. G01N 21/47
[52] U.S. Cl. .................................................. 356/446
[58] Field of Search ........................ 356/445, 446, 416

[56] References Cited

U.S. PATENT DOCUMENTS 4,632,559 12/1986 Brunsting ............................. 356/446
4,676,653 6/1987 Strohmeier et al. ................. 356/446

FOREIGN PATENT DOCUMENTS 148041 11/1981 Japan ..................................... 356/445

Primary Examiner—Richard A. Rosenberger
Attorney, Agent, or Firm—Roger N. Coe

[57] ABSTRACT

Reflectance apparatus is disclosed for obtaining measurement of nonspecular reflected light in which controlled light rays are directed along a transmission path from a light source through a plurality of light traps to expose or illuminate a specimen and nonspecular reflected light is passed from the specimen through the light traps along a transmission path to one or more detectors where the nonspecular reflected light is measured, the detector's field of view being larger than the illuminated area of the specimen over a wide range of specimen to source and detector distances.

6 Claims, 3 Drawing Sheets

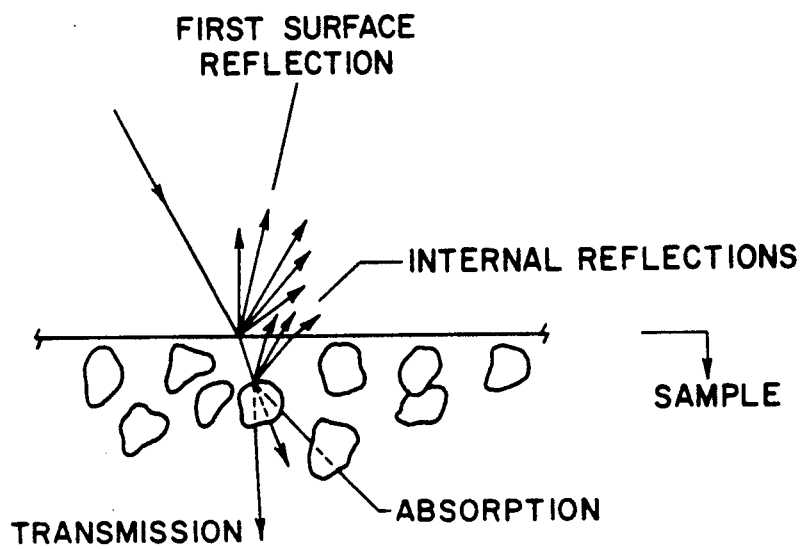
FIG. I
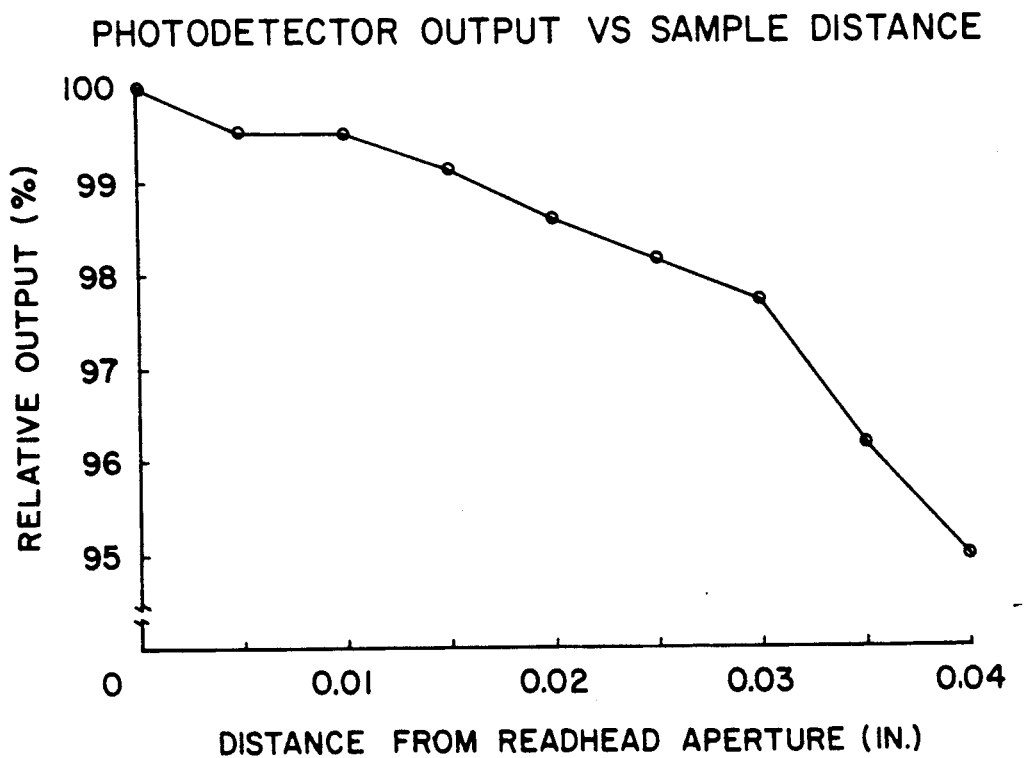
FIG. 4

READHEAD FOR REFLECTANCE MEASUREMENT OF DISTANT SAMPLES

BACKGROUND OF THE INVENTION

1. Field of the Invention

The present invention relates to an optical readhead for reflectance devices, and more particularly, to an accurate means of measuring diffuse, spectral reflectance over a wide variation in the distance between the sample and the illuminating source and detector

2. Description of the Prior Art

Analytical chemistry as a field of technology in connection with testing and determination of components in the presence of substances has rapidly been advanced in recent years, especially with regard to the specialized area of biochemistry which has emerged as a primary scientific frontier in modern times. There exists a need for increasingly sophisticated analytical methods and devices to make determinations involving new techniques which were never attempted heretofore. The explosion in the medical research field has encouraged the growth of the field of analytical chemistry with an emphasis on high precision, speed and simplicity in obtaining reproducible results. The growth and development of other industries such as brewing, chemical manufacturing and other have also resulted in rapid strides being made in the field of analytical chemistry.

A variety of analytical procedures, compositions and apparatus have been developed in order to meet the needs of these expanding fields and technologies including solution chemistry techniques, automated machinery and the so-called "dip and read" type reagent strips.

Because of their relatively low cost, ease of use and speed of obtaining results, reagent strip test devices enjoy wide popularity in many analytical applications, especially in the field of testing of biological fluids. In medicine and health areas, for example, numerous physiological functions and problems can be monitored and checked merely by dipping reagent test strips into a sample of body fluids such as urine and blood. By observing a detectable response, such as a change in color or a change in the amount reflected from or absorbed by these test devices, a particular health condition or body disfunction can be quickly determined even by persons who are not highly trained or skilled in the chemistry or medicinal technologies underlying these conditions. Many of these test devices produce a semi-quantitative detectable response and many efforts have been made to refine these devices to the point where almost quantitative results are obtained. For example, by measuring the response after a predetermined time, the analyst or observer can obtain not only a positive indication of the presence of a particular constituent or component in a test sample, but also an estimate of how much of the constituent is present, at least within parameters that provide the scientist or physician with an initial approximation of the problem or condition. Such test devices provide the physician with a facile diagnostic tool as well as the ability to rapidly and quickly gauge the extent of disease or body malfunction.

Many such test devices are currently available and are on the market including those available from the Ames Division of Miles Laboratories, Inc. under the proprietary designations CLINISTIX®, MULTISTIX®, DIASTIX®, DEXTROSTIX® and others.

Typically, test devices of the so-called dip and read type include one or more carrier matrices, such as bibulous paper or other absorbent material, having incorporated therein a particular reagent or reactive system which manifests a color change in the presence of a specific sample component. Depending on the reactant system incorporated into a particular matrix, these devices can detect the presence of glucose, ketones, bilirubin, urobilinogen, occult blood, nitrite and other substances. The specific time range after contacting the test device with sample is indicative of the presence of a particular component and the concentration in the sample. Some of these test devices and their reactant systems are set forth in U.S. Pat. Nos. 3,123,443; 3,212,855; 3,184,668; 3,164,534; 2,981,606; 3,298,789; 3,164,534; 3,092,465 and 2,981,606.

Automated instruments have been developed over a period of years which are intended to eliminate the need for manual manipulation of chemical reactants and which have programmed readouts which greatly facilitate and speed up such tests. Such devices are intended to improve reproducibility of tests by eliminating the subjectivity of the operator as a factor in obtaining reliable measurements. The emphasis on obtaining reliability and reproducibility of test results in today's climate of concern over accuracy and precision in laboratory test procedures is well known. Various reflectance instruments have been employed which use a light source and a photoelectric cell or other sensing means to determine color values by measuring the amount of light reflected from a colored surface illuminated by the reference light source.

One factor in being able to obtain reliable and accurate readings is the matter of positioning of the light source and the detector means in such a way as to minimize the effects of specular (that is mirror-like) reflections that occur at the surface of a test device being measured.

When dealing with reflectance measurement from surfaces of diagnostic reagent strip test devices, it is particularly important to avoid specular reflections and to obtain the measurement of nonspecular reflected light in the reflectance apparatus. Information on analyte concentration as a function of color development of a reagent test surface is contained only in the diffusely reflected energy. The specular component therefore represents a source of "noise" or inaccuracy in the reflectance measurement. As the state of the art moves toward more quantitative results, the ability to resolve small differences in reflectance—and hence small changes in analyte concentration—will in part be limited by the instrument's ability to suppress such "noise".

Some earlier efforts have been made to minimize the adverse affects of specular reflectance by changing the axis of detection relative to the axis of illumination. This is shown, for example, in U.S. Pat. Nos. 3,604,815 and 3,907,503. Other devices have proposed the use of multiple light sources positioned at an angle of 45° to the normal and collecting the reflected light normal to the specimen as shown in U.S. Pat. No. 4,279,514. The geometries involving a 45° angle have been considered most important in making reflection measurements as reported by the International Commission on Illumination publication CIE No. 44(TC2.3) 1979 entitled "Absolute Methods for Reflectance Measurements".

For the purpose of reducing or eliminating the adverse affects of specular reflection, previously described apparatus has been constructed which incorporates a diffusing chamber or integrating sphere; see for example U.S. Pat. No. 4,171,909. These designs do provide diffuse light to illuminate a specimen, however, the incorporation of an integrating sphere into such designs automatically increases the size and expense of the required optical readhead.

Textiles have often been the subject of reflectance measurement in order to analyze the surface thereof to determine certain properties of the textile. One such apparatus is shown in U.S. Pat. No. 4,033,698 which utilizes fiber optic bundles for transmittal of light to and from the textile sample area. This design appears to be quite costly and technically sophisticated However, the design does not appear to effectively minimize stray light rays originating from the light source and thus the adverse affects of specular reflectance.

Another optical system for analyzing the surface of a fibrous web is shown in U.S. Pat. No. 4,490,618 which analyzes the surface of paper or textile using a prism structure with one surface of the prism in contact with the fibrous web under a predetermined pressure. A collimated beam of light is directed into the prism on the contact surface. The light reflected from the contact surface to the prism is then directed to a detector.

Still a further example of use of a collimating lens to make the light rays substantially parallel for the purpose of testing the surface of a composition is shown in U.S. Pat. No. 3,776,642 where a testing device is used to determine the nature and characteristics of the surface of a quantity of grain to be analyzed.

In addition to the issue of included specular reflections, it is well known that the accuracy and precision of making diffuse reflectance measurements is highly dependent upon the distance from the test sample to the light source and the light detector. For example, if the sample moves farther away from the light source and detector, the magnitude of energy reaching the detector is decreased. To the instrument, this change in energy level is indistinguishable from an equivalent change due to color development of the sample.

This invention concerns the problem introduced by the translucency of a sample. The term "translucency" or "translucent" is defined as the property of transmitting some portion of the incident radiation.

SUMMARY OF THE INVENTION

In accordance with the present invention, there is provided an optical readhead for illuminating a reagent pad and obtaining the measurement of nonspecular reflected light wherein the light directed onto the sample is essentially collimated and the measurement of nonspecular reflected light is accurately obtained. The controlled light rays are directed along a transmission path from a light source through a plurality of light traps to expose or illuminate a specimen and the non-specular reflected light is passed from the specimen through the light trap and along a transmission path to one or more detectors without interference from the specular reflected light and where the nonspecular reflected light is measured. The design of the readhead of the present invention provides for the detector's field of view being larger than the illuminated area of the sample over a wide range of sample-to-source and sample-to-detector distances. Internal features of the readhead assembly suppress stray light reflections. The light trap is positioned between the light source and the specimen and between the specimen and the detector.

BRIEF DESCRIPTION OF THE DRAWINGS

Other and further advantages and features of the invention will be apparent to those skilled in the art from the following detailed description thereof, taken in conjunction with the accompanying drawings wherein:

FIG. 1 is a diagramatic representation illustrating a ray of light striking a translucent sample;

FIG. 4 is a plot of photodetector output versus sample distance.

DESCRIPTION OF THE PREFERRED EMBODIMENTS OF THE INVENTION

When dealing with translucent samples (material), some portion of the incident light energy will be reflected at the top surface of the sample, some portion of that incident light energy will be reflected by internal structure of the sample, some portion will be absorbed by the sample and some final portion of light will be transmitted. This is shown schematically in FIG. 1 illustrating that the major portion of the incident energy is reflected at the top surface, a significant portion of energy is the subject of internal reflections and some portion will be absorbed by the sample contents itself and finally, depending on the thickness etc., a small portion will be transmitted through the matrix specimen. What is clear from an understanding and analysis of the nature of a translucent matrix is that the energy reflected by the matrix does not come from any one surface but is the result of a volumetric effect which extends some depth into the matrix. Experiments have shown that the depth of this region is at least 0.010 inches (0.254 mm) on selected samples.

It is known that the exact volume that reflects energy will vary from sample to sample depending on many factors that affect the degree of translucency, such as, the refractive index, the spectral absorptivity, the size of the particles in the internal structure, the nature of those particles, the total sample thickness and the like. It is believed that variations in the depth from which energy is reflected from a translucent sample is indistinguishable from variations in the distance from the sample to the source and the detector. Therefore, reproducible positioning of the sample or matrix with respect to the source and the detector alone will not eliminate the error associated with materials of varying translucency.

Figure 2:
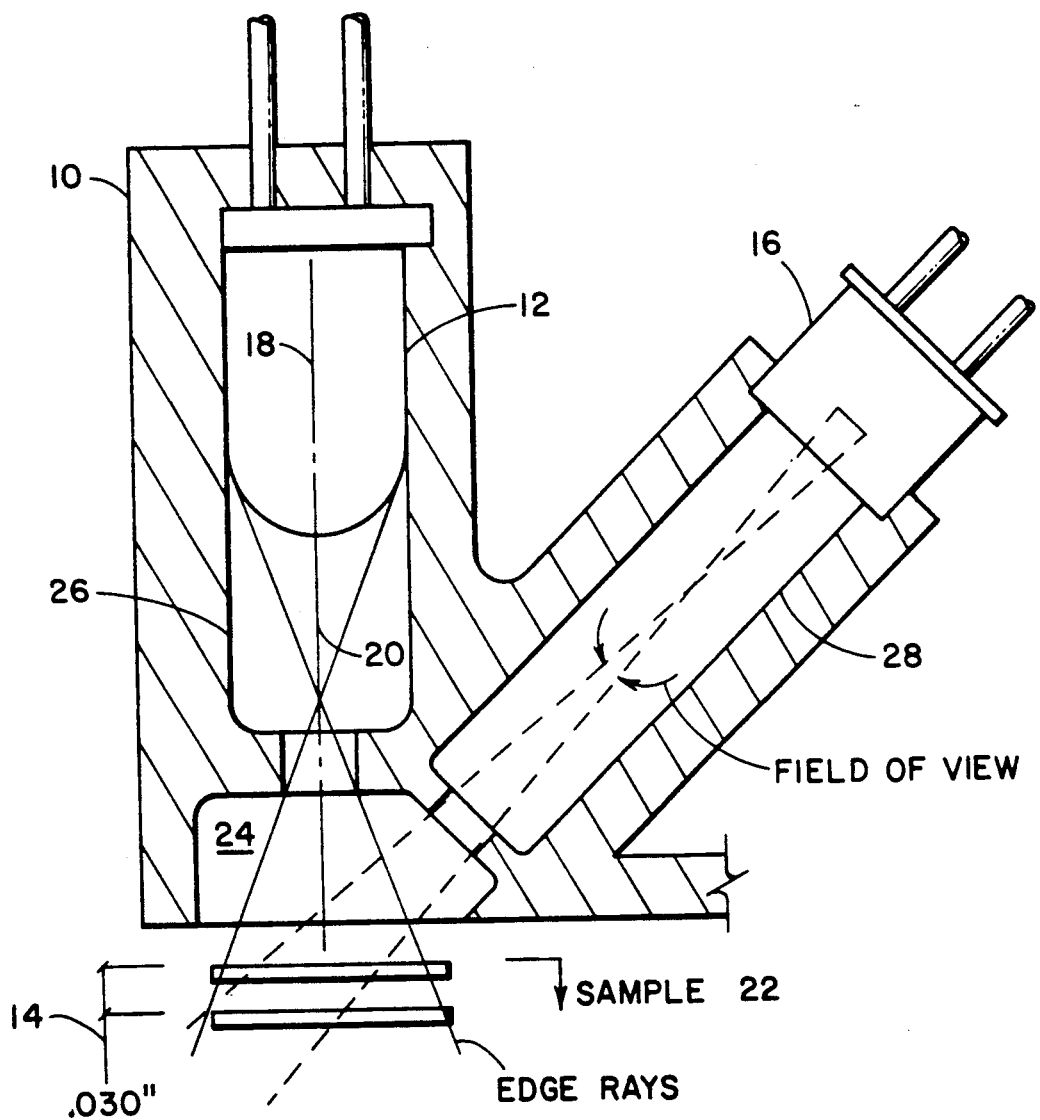
FIG. 2 is a cross-sectional plane view of prior art apparatus wherein the field of view of the detector is smaller than the illuminated area of the sample.

FIG. 2 shows a sectional view of a prior art reflectance measuring instrument. Many of such devices employ complex means of positioning the sample at a fixed and reproducible distance from the light source and the light detector. In this drawing, there is shown the apparatus 10 for the measurement of reflectance. This apparatus includes a light source 12, a specimen or sample holding area 14 and a reflected light detector 16. The axis of illumination 18 is parallel to an axis 20 that is normal to the specimen 22.

The device of the prior art 10 also typically has a light trap 24 positioned between the detector 16 and the sample 22. The precise configuration of the light trap 24 can vary widely provided that it is larger than the light transmission path 26 from the light source 12. The walls of the light trap are arranged in such a configuration that they are not directly illuminated by the light source 12. Light traps function to prevent the stray light from passing to the detector 16 and also to prevent the specular rays from passing from the samples 22 to the detector 16. The term "stray light" is defined herein as energy reaching the detector that has been reflected from surfaces other than the sample. The light trap also functions to reduce secondary rays from any baffles 27 that may exist in the light transmission path as the light rays pass from the light source through the light transmission path 26 to illuminate the specimen 22 and then pass from the specimen through another light transmission path 28 back to the detector 16. Typically, the light trap is coated with dull black paint and can also contain baffles to help suppress the stray light.

As shown in FIG. 2 as the sample 22 moves further away from the source 12 and the detector 16, the detector field of view, which is indicated by the dashed lines, increases to receive more reflected energy from a different area of the sample. In order for the reflected energy to remain constant, the sample would need to be constrained to have a homogeneous surface. Thus, any variations or changes in the nature of the surface would then change the nature of the readings. Moreover, as the sample in FIG. 2 moves away from light source 12, the sample area within the detector field of view is illuminated by a different portion of the source output beam 12. This is indicated by the solid ray lines emanating from source 12 in FIG. 2. Thus, in order for the reflected energy to remain constant, the source output would have to be spatially uniform.

Figure 3:
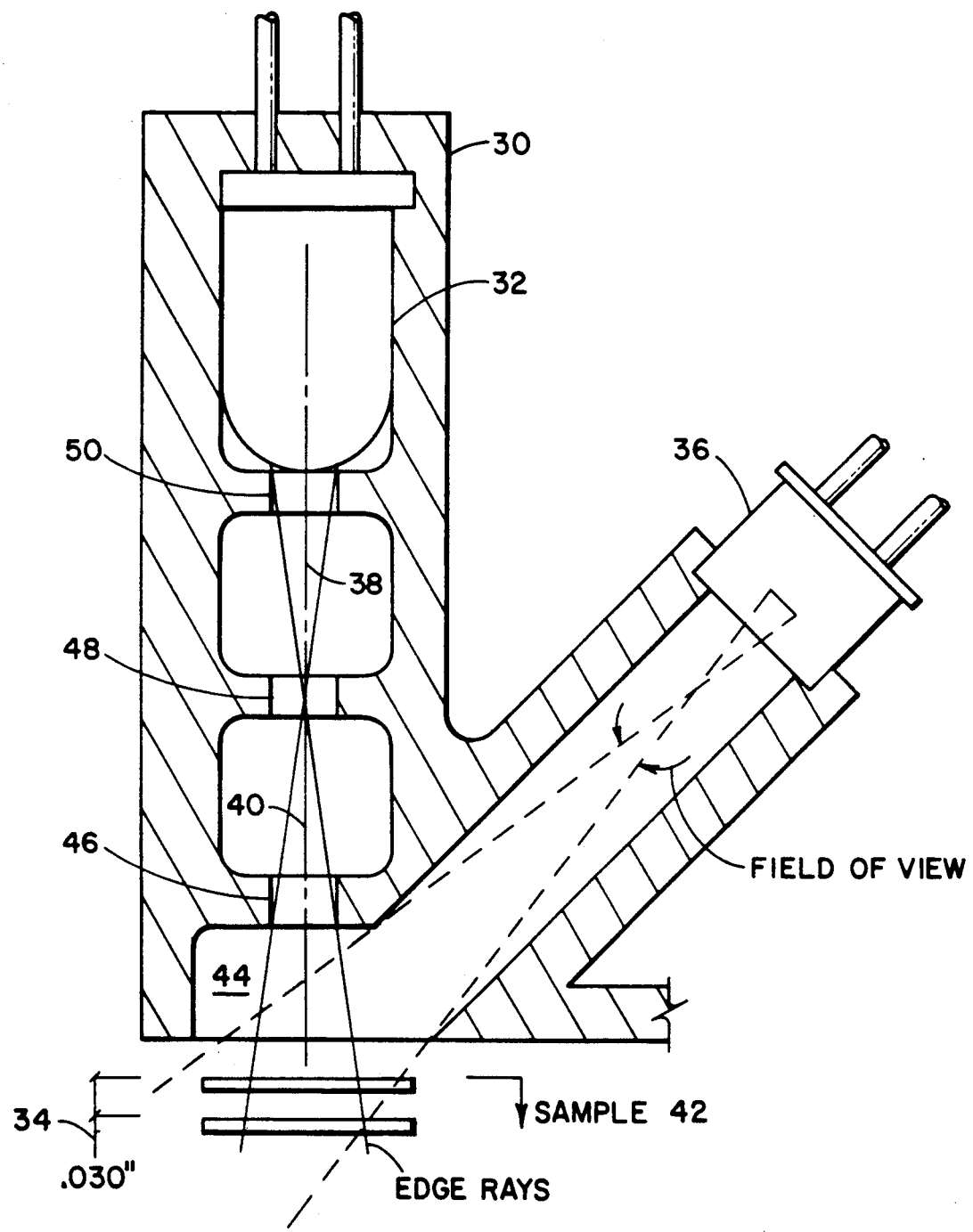
FIG. 3 is a cross-sectional plane view of an apparatus in accordance with the present invention which illustrates that the field of view of the photodetector is larger than the illuminated area of the sample.

FIG. 3 illustrates the device of the present invention which includes a reflectance device 30 composed of a light source 32, a specimen holding area 34 and a photodetector 36. Typically, the photodetector and the light source are at an angle to each other such as 45°. The axis of illumination 38 is parallel to the axis 40 which is normal to the specimen 42.

In accordance with the present invention, the reflectance device 30 has a light trap 44 positioned between the photodetector 36 and the sample 42. As previously stated, the precise configuration of the light trap is not critical provided that it is larger than the aperture 46 in the light path from the light source 32 to the specimen 42 such that the walls of the light trap are not directly illuminated by the light source 32. Light trap 44 thus functions to prevent stray light from passing to photodetector 36 from the surface of sample 42 and also to prevent specular rays from passing from the specimen to the detector 36 and for any other incident reflections. As shown in FIG. 3, a number of apertures 46, 48 and 50 are interposed between the source 32 and sample 42. The function of these apertures is to limit the sample area that is illuminated by source 32 and to provide a nearly collimated illumination. It has been found that a beam divergence of no larger than about 8° is sufficient for the application. This is shown by the solid lines in FIG. 3 hitting the surface of sample 42. This is intended to ensure that substantially the same sample area is illuminated for a wide range of sample-to-source distances. Thus, for example, as the sample moves 0.100 inches (2.54 mm) in FIG. 3, the illuminated diameter increases less than 20%. In addition, it is clear that the sample is always illuminated from the same spatial points of the source output.

The detector 36 field of view is relatively unrestricted. The design is such that the sample can be moved in FIG. 3 and the detector field of view increases to totally include energy reflected from the increasing illumination area.

As shown in FIG. 3, a single wavelength can be conveniently used as source 32. Typically, this can be a high output, lens-ended light emitting diode (LED) as the source and a silicon photodetector 36 as the receiver which can be conveniently contained in a molded black plastic housing. An alternative design is to use an incandescent lamp as the source in conjunction with an appropriate filter (not shown) for wavelength selection to be oriented in front of the photodetector 36.

The invention lends itself easily to measurements at multiple wavelengths. In this case, the LED would be replaced by a device with multiple emitting elements wherein each element would be of a different wavelength. Alternatively, if an incandescent lamp is used as the source, a discrete filter and photodetector would be replaced by a single package containing multiple filter photodetector pairs.

A plot of detector output versus sample distances is given in FIG. 4 and as shown for a change in sample distance from source and detector out to 0.030 inches (0.76 mm), the reflected energy changes less than 2%.

In the apparatus of the invention, there are no illumination rays which first strike internal surfaces of the readhead and are reflected directly into the detector. If any specular components are reflected back into the readhead from the sample surface, their affect is minimized because the readhead has been designed to be of low reflectance material and can incorporate multiple traps such that all specular rays must undergo multiple reflections before they reach the detector Thus, the magnitude of any stray energy at the detector is reduced to insignificant levels.

The specific light source and detector whether singular or a plurality that are used in accordance with the invention can vary widely. A preferred light source is a light emitting diode (LED) model HLMP-3950 made by Hewlett-Packard Components of Palo Alto, Calif. It will be understood, however, that the light source can be any suitable incandescent or nonincandescent light source provided a lens is employed to focus the light. Moreover, the light source can be frosted or used with diffused means to cause diffuse illumination of the specimens. A suitable detector is Model SD-041-11-11-011-(isolated)-211 which is made by Silicon Detector Corporation of Newbury Park, Calif. A filter can, if desired, be placed in front of the detector.

A lens can be interposed between the source and the sample as may be convenient to focus much of the light over a short distance and to maximize the light that is available to illuminate the specimen provided it is in an essentially collimated form. In addition, the lens can serve to control light transmitted to the specimen so as to minimize stray light which will interfere with measurements being taken.

The material used in construction of the optical readhead of the invention is not critical and any suitable opaque material such as metal or plastic can be employed. Preferably, the optical readhead is constructed of molded black plastics such as an acrylonitrile-butadiene-styrene copolymer, polymethyl methacrylate, polystyrene, polyethylene and the like. As indicated above, the configuration of the light trap can be varied but the light trap surfaces should not be directly illuminated by the light source employed. In accordance with the configuration of the invention, the light transmission paths of the present invention substantially eliminate stray light from illuminating the surface of the specimen.

By designing apparatus in accordance with the present invention, small inexpensive and reliable reflectance devices can be constructed. Thus, size and cost can be reduced significantly in comparison with some commercially available devices.

The present invention is well adapted to attain all of the objects and features hereinabove set forth together with other advantages which are obvious and which are inherent to the system. The features of the invention can be of a particular importance in suppressing stray light reflections in a device which is convenient, simple, relatively inexpensive, effective and reliable.

It should be understood that other variations and modifications will be apparent to those skilled in the art from the foregoing and can be made without departing from the spirit and scope thereof.

Use of multiple detectors, reversal in position of the light source path and detector path, the use of light sources differing in transmitted wavelength, the use of filters to limit the light source transmitted or the reflected light detected and many other features are variations within the skill of those in the art to which this invention is addressed. These and other modifications and variations of the invention as hereinabove set forth can be made without departing from the spirit and scope thereof.

What is claimed is:

1. An apparatus for measuring reflected light which comprises a light source, means separated at varying distances from such apparatus for supporting a specimen having a surface the reflectance of which is to be measured upon exposure to light emitted from said light source, and means for detecting light reflected from the surface of the specimen, means for passing light rays through and along a transmission path and through at least one light trap to illuminate the specimen and to measure nonspecular reflected light passed from the specimen through said light trap wherein said light source impinges on said sample in essentially collimated rays whose divergence is 8° or less and wherein the field of view of the means for detecting light is larger than the illuminated area of said specimen.

2. The apparatus as set forth in claim 1 in which the specimen is adapted to be mounted in means that can change in distance from the light source.

3. The apparatus as set forth in claim 1 in which the light source is a light emitting diode.

4. The apparatus as set forth in claim 1 in which the light source is an incandescent lamp.

5. The apparatus as set forth in claim 1 wherein the light source has a diffusing surface.

6. The apparatus as set forth in claim 1 which has a plurality of windows through which the light source passes before illuminating the specimen.

* * * * *